United States Patent [19]
Katano et al.

[11] Patent Number: 6,063,779
[45] Date of Patent: May 16, 2000

[54] 5-(4-PIPERIDINYL)DIBENZOTHIAZEPINE DERIVATIVES AND 5-(4-PIPERIDINYL) DIBENZOXAZEPINE DERIVATIVES, AND ANTIARRHYTHMIC AGENTS

[75] Inventors: Kiyoaki Katano; Takahiko Satoh; Tomoko Soneda; Naoko Kamitoh; Kazuyuki Fujishima; Mitsugu Hachisu, all of Yokohama, Japan

[73] Assignee: Meiji Seika Kaisha, Ltd., Tokyo-To, Japan

[21] Appl. No.: 09/079,861

[22] Filed: May 15, 1998

[30] Foreign Application Priority Data

May 15, 1997 [JP] Japan ..................... 9-124608

[51] Int. Cl.⁷ ................ A61K 31/55; C07D 267/02; C07D 281/02
[52] U.S. Cl. ...................... 514/211; 540/550
[58] Field of Search .................. 514/211; 540/550

[56] References Cited

U.S. PATENT DOCUMENTS 3,631,052 12/1971 Yale et al. ............. 260/293.58
3,796,725 3/1974 Yale et al. ............. 260/333
4,888,335 12/1989 Mohrbacher et al. .......... 514/217

FOREIGN PATENT DOCUMENTS 0026469 4/1981 European Pat. Off. .

Primary Examiner—Mukund J. Shah
Assistant Examiner—Brenda Coleman

Attorney, Agent, or Firm—Wenderoth, Lind & Ponac LLP

[57] ABSTRACT

An objective of the present invention is to provide a compound that has antiarrhythmic activity. The present invention provides a compound of formula (I):

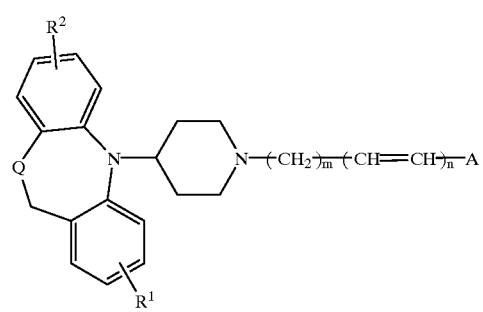

wherein $R^1$ and $R^2$ each represent H, halogen or lower alkyl which may be substituted by halogen; A represents H, C3–6 cycloalkyl, phenyl which may be substituted by halogen, nitro, or lower alkoxy, a 5-membered or 6-membered heterocyclic ring which may contain N and/or S, —$NR^3R^4$ (wherein $R^3$ and $R^4$ each represent H or lower alkyl which may be substituted by phenyl), or $COR^5$ (wherein $R^5$ represents OH, amino or lower alkoxy); Q represents S or O; m represents 0–18; and n represents 0–2, and pharmaceutically acceptable salts and solvates thereof.

9 Claims, No Drawings

5-(4-PIPERIDINYL)DIBENZOTHIAZEPINE DERIVATIVES AND 5-(4-PIPERIDINYL) DIBENZOXAZEPINE DERIVATIVES, AND ANTIARRHYTHMIC AGENTS

BACKGROUND OF THE INVENTION

1. Field of the Invention

The present invention relates to 5-(4-piperidinyl) dibenzothiazepine and 5-(4-piperidinyl)dibenzoxazepine derivatives and antiarrhythmic agents.

2. Background Art

Clinical tests conducted in Europe and the United States have revealed that antiarrhythmic agents should be used carefully. However, the pharmacotherapy may be still effective to treat arrhythmic patients that have a risk of sudden death, symptoms deleteriously affecting cardiovascular movement, symptoms seriously damaging the quality of life due to severe pain, and symptoms causing embolism in organs due to intracardiac thrombosis.

Antiarrhythmic agents include sodium channel blockers, β-blockers, potassium channel blockers, and calcium antagonists. However, a need still exists for an effective and safe agent for the treatment of arrhythmia.

SUMMARY OF THE INVENTION

An object of the present invention is to provide a compound that has antiarrhythmic activity.

Another object of the present invention is to provide an antiarrhythmic agent.

The present invention provides a compound of formula (I):

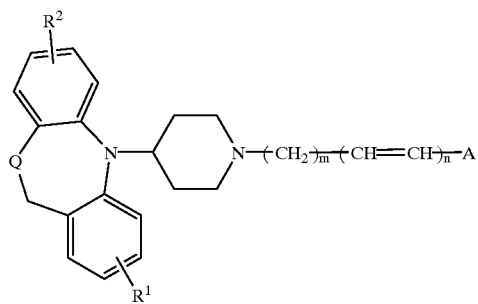

wherein $R^1$ and $R^2$, which may be the same or different, each represent hydrogen, halogen or lower alkyl which may be substituted by halogen;

A represents hydrogen, $C_{3-6}$ cycloalkyl, phenyl, a saturated or unsaturated 5-membered or 6-membered heterocyclic group which may contain one or more heteroatoms selected from a nitrogen, sulphur and oxygen atom, $-NR^3R^4$ (wherein $R^3$ and $R^4$, which may be the same or different, each represent hydrogen or lower alkyl which may be substituted by halogen or phenyl), or $-COR^5$ (wherein $R^5$ represents hydroxyl, amino or lower alkoxy which may be substituted by halogen), and where the $C_{3-6}$ cycloalkyl group, the phenyl group and the heterocyclic group each may be substituted by one or more substituents selected from halogen, nitro, and lower alkoxy which may be substituted by halogen;

Q represents an oxygen or sulphur atom;

m represents an integer from 0 to 18; and n represents zero, 1 or 2, and pharmaceutically acceptable salts and solvates thereof.

The compounds according to the present invention are useful as an antiarrhythmic agent.

DETAILED DESCRIPTION OF THE INVENTION

Compounds

The term "lower alkyl" or "lower alkoxy" as a group or a part of a group refers to a straight or branched chain alkyl group or alkoxy group which has 1–6 carbon atoms, preferably 1–4 carbon atoms. The term "$C_{3-6}$ cycloalkyl" refers to a monocyclic alkyl group which has 3–6 carbon atoms.

The term "halogen" refers to a fluorine, chlorine, bromine or iodine atom.

Examples of lower alkyl include methyl, ethyl, n-propyl, i-propyl, n-butyl, i-butyl, s-butyl, t-butyl, n-pentyl and n-hexyl.

One or more hydrogen atoms in the lower alkyl group can be substituted by halogen. Examples of such substituted lower alkyl include trifluoromethyl, 2-fluoroethyl, difluoroethyl, 2,2,2-trifluoroethyl, trichloromethyl, 2-chloroethyl, dichloroethyl, 1,1,1-trichloromethyl, tribromomethyl, 2-bromoethyl, dibromoethyl, 1,1,1-tribromoethyl, pentafluoroethyl, fluoromethyl, 3,3,3-trifluoropropyl, 4,4,4-trichlorobutyl, 5,5,5-trifluoropentyl and 6,6,6-trifluorohexyl.

One or more hydrogen atoms in the lower alkyl group may be substituted by phenyl. Examples of such substituted lower alkyl include benzyl (Bn) and phenethyl.

Examples of lower alkoxy include methoxy, ethoxy, n-propoxy, i-propoxy, n-butoxy, i-butoxy, s-butoxy and t-butoxy.

One or more hydrogen atoms in the lower alkoxy group may be substituted by halogen. Examples of such substituted alkoxy include 2,2,2-trifluoroethoxy, difluoroethoxy, 2,2,2-trichloroethoxy, dichloroethoxy, dibromoethoxy, 2,2,2-tribromoethoxy, fluoromethoxy, difluoromethoxy, trifluoromethoxy, 2-bromoethoxy, 4,4,4-trifluorobutoxy, pentafluoroethoxy and 3,3,3-trifluoropropoxy.

Examples of $C_{3-6}$ cycloalkyl include cyclopropyl, cyclobutyl, cyclopentyl and cyclohexyl.

Examples of a saturated or unsaturated 5-membered or 6-membered heterocyclic group include pyridine, thiophene, thiazole, pyrrole, furan, imidazole, oxazole, pyrimidine and pyrazine.

$R^1$ and $R^2$ preferably each represent hydrogen.

A preferably represents hydrogen, cyclohexyl, phenyl, p-fluorophenyl, (3-methoxy-2-nitro)phenyl, pyridinyl, thiophenyl, $-N(CH(CH_3)_2)_2$, $-N(Bn)_2$ (wherein Bn represents benzyl), $-COOH$, $-COOCH_2CH_3$, or $-CONH_2$.

Examples of preferred compounds according to the present invention are those wherein A represents hydrogen, C3–6 cycloalkyl, phenyl which may be substituted by one or more substituents selected from halogen, nitro, and lower alkoxy, a saturated or unsaturated 5-membered or 6-membered heterocyclic ring which may contain a nitrogen or sulphur atom or a combination thereof, $-NR^3R^4$ (wherein $R^3$ and $R^4$, which may be the same or different, each represent hydrogen or lower alkyl which may be substituted by phenyl), or $COR^5$ (wherein $R^5$ represents hydroxyl, amino or lower alkoxy);

Q represents a sulphur atom;

m represents an integer from 0 to 18; and n represents zero, 1 or 2.

Examples of preferred compounds of the present invention include:

5-[1-(4-cyclohexyl-1-butyl)piperidine-4-yl]-5,11-dihydro dibenz[b,e][1,4]thiazepin, 5-(1-cinnamylpiperidine-4-yl)-5,11-dihydrodibenz[b,e][1,4] thiazepin, 5,11-dihydro-5-[1-(N,N-dibenzylaminoethyl)piperazine-4-yl]dibenz[b,e][1,4]thiazepin, 5,11-dihydro-5-[1-(3-methoxy-2-nitro)cinnamylpiperidine-4-yl]dibenz[b,e][1,4]thiazepin, 5-[1-(4-cyclohexyl-1-butyl)piperidine-4-yl]-5,11-dihydrodibenz[b,e][1,4]oxazepin, 5-(1-cinnamylpiperidine-4-yl)-5,11-dihydrodibenz[b,e][1,4] oxazepin, 5,11-dihydro-5-[1-(N,N-dibenzylaminoethyl)piperazine-4-yl]dibenz[b,e][1,4]oxazepin, and 5,11-dihydro-5-[1-(3-methoxy-2-nitro)cinnamylpiperidine-4-yl]dibenz[b,e][1,4]oxazepin.

The pharmaceutically acceptable salts of the compound of formula (I) include pharmaceutically acceptable nontoxic salts, for example, inorganic salts such as sodium, potassium, magnesium and calcium salts; acid addition salts formed with pharmaceutically acceptable acids such as trifluoroacetic acid, hydrochloric acid, sulfuric acid, methanesulfonic acid and citric acid; and amino acid salts formed with acids such as glutamic acid and aspartic acid.

The pharmaceutically acceptable solvates of the compound of formula (I) include hydrates and ethanol solvates.

The compound of formula (I) may be an optical isomer. All isomers of the compound of formula (I) and mixtures thereof including racemic mixtures are included within the scope of the present invention.

Process for Preparing the Compound

The compound of the present invention can be synthesized according to the following scheme.

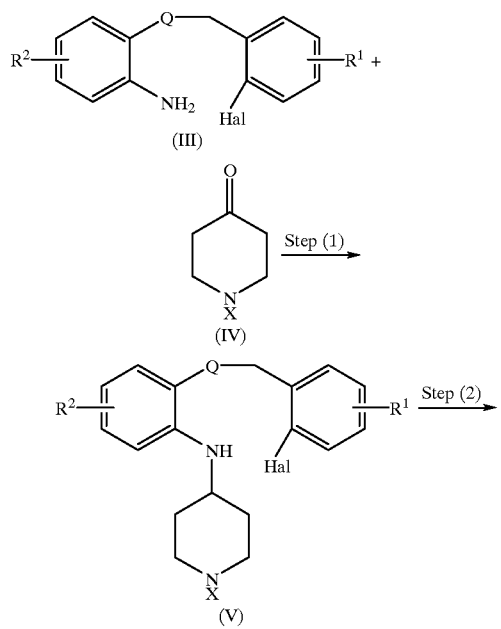

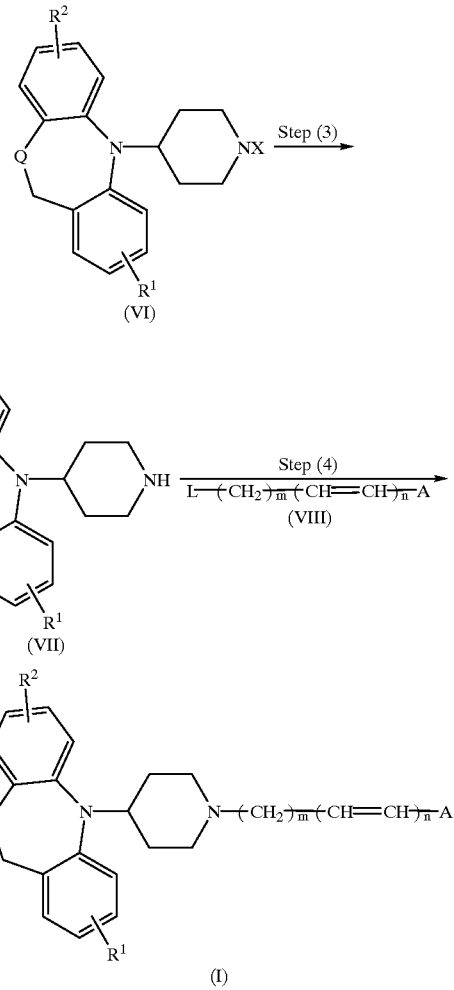

wherein

Q, $R^1$, $R^2$ and A are as defined in formula (I), Hal represents halogen, X represents a protecting group of an amino group, L represents halogen, lower alkylsulfonyloxy, allylsulfonyloxy, and formyl, m and n are as defined in formula (I), provided that when L represents formyl, m denotes an integer from 0 to 17.

In step (1), the compound of formula (III) is reacted with the compound of formula (IV) to give the compound of formula (V) by the reducing alkylation reaction according to the method described in J. Med. Chem., 15, 713 (1970). The reaction can be performed in an inert solvent such as 1,2-dichloroethane, dichloromethane, chloroform, ethyl acetate, dioxane, or tetrahydrofuran in the presence of a reducing agent such as sodium borohydride, sodium triacetoxyborohydride, or sodium cyanoborohydride, or a catalyst such as palladium-carbon, palladium black, or platinum oxide for catalytic reduction, followed by the reaction in the presence or absence of an acid such as acetic acid, formic acid, or hydrochloric acid at a temperature between −20 and 100° C. for 30 minutes to 24 hours, preferably in the presence of an acid at a temperature between 0 and 80° C. for 1 to 10 hours.

X in the compound of formula (IV) may be an amino protecting group such as tert-butoxycarbonyl, trifluoroacetyl or acetyl which is described in, for example, Nobuo Izumiya, "Basis and Experimentals of Peptide Synthesis", Maruzen K. K.

In step (2), the compound of formula (V) is converted to the compound of formula (VI). The reaction is performed in an inert solvent such as pyridine, N,N-dimethyl formamide, N,N-dimethylacetamide, dimethylsulfoxide, or dioxane in the presence of metal powder such as copper or iron, and a base such as potassium carbonate, sodium carbonate, potassium hydroxide, or sodium hydroxide at a temperature between 30 and 250° C. for 1 hour to 1 week, preferably at a temperature between 50 and 200° C. for 3 hours to 5 days.

In step (3), the protecting group X in the compound of formula (VI) is removed to give the compound of formula (VII). The reaction can be performed according to the method described in, for example, Nobuo Izumiya, "Basis and Experimentals of Peptide Synthesis", Maruzen K. K.

In step (4), the compound of formula (I) is obtained by the alkylation or reducing alkylation reaction of the amino group in formula (VII) with the compound of formula (VIII). The alkylation reaction can be performed in a solvent which is not involved in the reaction such as acetone, methyl ethyl ketone, N,N-dimethylformamide, dimethylsulfoxide, 1,2-dichloroethane, dichloromethane, chloroform, ethyl acetate, dioxane, or tetrahydrofuran in the presence of a base such as an organic base, for example, pyridine, triethylamine, diisopropylethylamine, 4-dimethylaminopyridine, or N-methylmorpholine, or an inorganic base, for example, potassium carbonate, sodium carbonate, potassium hydroxide, sodium hydroxide, potassium hydrogen carbonate, or sodium hydrogen carbonate at a temperature between −20 and 200° C. for 30 minutes to 48 hours, preferably at a temperature between −10 and 150° C. for 1 to 30 hours. The reducing alkylation can be performed according to step (1).

Alkylsulfonyloxy having 1–4 carbon atoms which may be represented by L in formula (VIII) includes methanesulfonyloxy, ethanesulfonyloxy and n-butanesulfonyloxy. Allylsulfonyloxy which may be represented by L in formula (VIII) includes benzenesulfonyloxy and p-toluenesulfonyloxy.

Use/Pharmaceutical Compositions

The compound of formula (I) has been shown to have antiarrhythmic activity in ischemic reperfusion arrhythmic model rat. The rat is known as human arrhythmic models (Proceeding of Society for Experimental Biology and Medicine, 191, pp201–209(1989)). The compound of formula (I) and pharmacologically acceptable salts and solvates thereof are therefore useful in the treatment of arrhythmia. The term "treatment" as used herein also refers to "prevention".

The compound according to the present invention can be administered to a human and other animals orally or parenterally, for example, intravenously, intramuscularly, subcutaneously, rectally or percutaneously.

The compound according to the present invention can be formulated in a form suitable for administration, for example, intravenous injections and intramuscular injections for parenteral administration, capsules, tablets, granules, dispersible powders, pills, fine particles and troches for oral administration, rectal agents, oily suppositories and aqueous suppositories for rectal administration.

The above pharmaceutical formulations can be prepared using conventional excipients (e.g., binding agents and fillers), vehicles (e.g., solvents, diluents), adjuvants (e.g., solubilizing agents, emulsifying agents, suspending agents, disintegrating agents, lubricants, tonicity agents, wetting agents, dispersing agents, buffering agents and solution adjuvants), and additives (e.g., antioxidants, preservatives, pH controlling agents, flavorings, soothing agents, stabilizing agents, colorants and sweetening agents). Examples of possible nontoxic carriers to be used include lactose, fructose, glucose, starch, gelatin, magnesium carbonate, synthetic magnesium silicate, talc, magnesium stearate, methylcellulose or salts thereof, gum arabic, polyethylene glycol, syrup, vaseline, glycerine, ethanol, propylene glycol, citric acid, sodium chloride, sodium sulfite and sodium phosphates.

The composition may contain about 1–70% by weight, preferably about 5–50% by weight, of the compound of the present invention depending on the dosage form. A dosage can be appropriately determined depending on the route of administration, the age and sex of the patient, the severity of the condition to be treated. A proposed dosage for the treatment of arrhythmia is about 0.1–1000 mg/kg body weight per day, preferably 1–200 mg/kg body weight per day. The unit dose may be administered one or several times per day.

EXAMPLES

The present invention is further illustrated by the following Examples which are not intended as a limitation of the invention.

Preparation 1

2-(2-bromobenzyl)thio-N-(1-tert-butyloxycarbonyl-4-piperidinyl)aniline

To a solution of 2-(2-bromobenzyl)thioaniline (7.55 g) and 1-tert-butyloxycarbonylpiperidin-4-one (6.68 g) in 2-dichloroethane (100 ml) were added acetic acid (30 ml) and sodium triacetoxyborohydride (7.1 g), and the mixture was stirred at a room temperature for 2 hours. Additional amount of sodium triacetoxyborohydride (500 mg) was added, and the mixture was further stirred at a room temperature for 2 hours. The reaction was concentrated under reduced pressure, diluted with ethyl acetate, washed successively with water, a saturated aqueous sodium hydrogen carbonate solution, and water, dried over magnesium sulfate, and the solvent was removed. The residue thus obtained was purified by chromatography on a silica gel column (250 g) to give the title compound as a resinous product (11.2 g, 91%) from the fraction eluted with n-hexane:ethyl acetate= 5:1.

$^1$HNMR(CDCl$_3$)δ: 2.24–2.35(2H,m), 1.48(9H,s), 1.85–1.95(2H,m), 2.95(2H,brt.,), 3.36(1H,m), 3.38–4.02 (2H,m), 3.95(2H,s), 5.0 7(1H,d,J=8.0), 6.55(1H,d,J=7.7), 6.57(1H,dd), 6.91(1H,dd, J=2.2, 7.1), 7.05–7.12(2H,m), 7.17(1H,dd,J=1.5, 7.7), 7.30(1H,dd,J=1.7, 8.1), 7.53(1H,dd, J=1.9, 7.5); TSIMS(m/z):477,479(M+H)$^+$ Preparation 2

5-(1-tert-butyloxycarbonylpiperidin-4-yl)-5,11-dihydrobenz[b,e][1,4]thiazepine

To a solution of the compound of Preparation 1 (11.2 g) in pyridine (120 ml) were added copper powder (1.54 g) and potassium carbonate (9.4 g), and the mixture was heated under reflux for 3 days. The reaction was diluted with ethyl acetate, and insolubles were removed by filtration through celite. The filtrate was concentrated under reduced pressure, diluted with ethyl acetate, and insolubles were removed by filtration through celite. The filtrate was washed with water, dried over magnesium sulfate, and concentrated. The residue thus obtained was purified by chromatography on a silica gel column (250 g) to give the title compound as a resinous product (8.32 g, 90%) from the fraction eluted with n-hexane:ethyl acetate=4:1.

¹HNMR(CDCl₃)δ: 1.35–1.49(10H), 1.53–1.64(1H,m), 1.78–1.88(1H,m), 2.05–2.15(1H,m), 3.01–3.17(2H,m), 3.38 (1H,d,J=12.0), 3.63–3.72(1H,m), 3.84–3.93(1H,m), 4.05–4.13(1H,m), 5.28(2H,d,J=12.0), 6.84(1H,dt,J=1.4,7.5), 6.97–7.03(2H,m), 7.11–7.18(3H,m), 7.24(1H,dd,J=1.6,7.5); TSIMS(m/z):397(M+H)⁺

Example 1

5-(piperidin-4-yl)-5,11-dihydrodibenz[b,e][1,4]thiazepine

To a solution of the compound of Preparation 2 (8.1 g) in dichloromethane (60 ml) were added anisole (3 ml) and trifluoro-acetic acid (5 ml) under ice-cooling, the mixture was stirred at a room temperature for 4 hours before addition of an additional amount of trifluoroacetic acid (5 ml) and stirring for 1 hour. The reaction was concentrated under reduced pressure, diluted with water, and acidified with IN hydrochloric acid. The aqueous solution was washed with ether, the ether layer was diluted with n-hexane and extracted with water, and the extract was combined with the aqueous layer. The combined aqueous layer was adjusted to an alkaline pH with 1N sodium hydroxide, extracted with ether, dried over magnesium sulfate, and concentrated. The residue thus obtained was diluted with n-hexane:ether (1:1, 10 ml), and stirred overnight at room temperature, and the precipitated crystalline product was collected by filtration and dried to give the title compound (4.94 g, 82%).

¹HNMR(CDCl₃)δ: 1.22–1.33(1H,m), 1.42–1.61(2H,m), 1.87(1H,brd), 2.21(1H,brd), 2.61–2.75(2H,m), 3.00(1H,m), 3.13(1H,m), 3.37(1H,d,J=12.1), 3.94–4.03(1H,m), 5.35(1H, d,J=12.1), 6.83(1H,m), 6.96–7.02(2H,m), 7.10–7.17(3H,m), 7.24(1H,m), 7.31(1H,d,J=7.5); ESIMS(m/z):297(M+H)⁺

Example 2

5-[1-(4-cyclohexyl-1-butyl)piperidin-4-yl]-5,11-dihydro-benz[b,e][1,4]thiazepine To a solution of the trifluoroacetic acid salt of the compound of Example 1 (255 mg) in N,N-dimethylformamide (3 ml) were added 1-cyclohexyl-4-p-toluenesulfonyloxybutane (183 mg) and potassium carbonate (405 mg), and the mixture was stirred at 90° C. for 6 hours before addition of an additional amount of 1-cyclohexyl-4-p-toluenesulfonyloxybutane (200 mg) and stirring at the same temperature for 6 hours. The reaction was diluted with ethyl acetate, washed with water, dried over magnesium sulfate, and the solvent was evaporated. The residue thus obtained was purified by chromatography on a silica gel column to give the title compound (184 mg, 87%).

¹HNMR(CDCl₃)δ: 0.79–0.91(2H,m), 1.08–1.33(9H,m), 1.39–1.51(3 H,m), 1.58–1.75(6H), 1.87(1H,brd) 2.04–2.23 (2H,m), 2.26–2.33 (2H,m), 2.69(1H,brs), 2.87(1H,m), 3.35 (1H,d,J=12.0), 3.91(1H,m), 5.34(1H,d,J=12.0), 6.82(1H,m), 6.96–7.03(2H,m), 7.10–7.19(3H,m), 7.23(1H,m), 7.30(1H, dd,J=1.4,7.4); TSIMS(m/z):435 (M+H)⁺

The compounds of Examples 3 to 14 were synthesized according to the procedure described in Example 2.

Example 3

5-(1-benzylpiperidin-4-yl)-5,11-dihydrodibenz[b,e][1,4]-thiazepine

¹HNMR(CDCl₃)δ: 1.49(1H,m), 1.65(1H,m), 1.86(1H,m), 2.18(3H,m), 2.64(1H,m), 2.85(1H,m), 3.32(1H,d,J=12.0), 3.54(2H,s), 3.93 (1H,m), 5.28(1H,d,J=12.0), 6.81(1H,m), 6.97(2H,m), 7.12(3H,m), 7.19–7.32(7H,m); FABMS(m/z):387(M+H)⁺

Example 4

5-(1-cinnamylpiperidin-4-yl)-5,11-dihydrodibenz[b,e][1,4]-thiazepine

¹HNMR(CDCl₃)δ: 1.53(1H,m), 1.72(1H,m),1.91(1H,m), 2.20(3H,m), 2.74(1H,m), 2.93(1H,m), 3.18(2H,d,J=6.7), 3.35(1H, d, J=12.0), 3.96(1H,m), 5.34(1H, d, J=12.0), 6.28 (1H,m), 6.51(1H, d, J=16), 6.82(1H,m), 6.98(2H,m), 7.13 (3H,m), 7.20–7.37(7H,m) FABMS(m/z):413(M+H)⁺

Example 5

5,11-dihydro-5-[1-(N,N-di-iso-propylaminoethyl)piperidin-4-yl]dibenz[b,e][1,4]thiazepine ¹HNMR(CDCl₃)δ: 1.04(12H), 1.48(1H,m), 1.67(1H,m), 1.92(1H,m), 2.22(3H,m), 2.45(2H,m), 2.61(2H,m), 2.76 (1H,m), 2.95(1H,m), 3.05(1H,m), 3.36(1H, d, J=12), 3.93 (1H,m), 5.33(1H, d, J=12), 6.83(1H,m), 6.98(2H,m), 7.13 (2H,m), 7.21–7.31(3H,m) EIMS(m/z):423(M)⁺;

Example 6

5,11-dihydro-5-[1-(N,N-dibenzylaminoethyl)piperidin-4-yl]-dibenz[b,e][1,4]thiazepine ¹HNMR(CDCl₃)δ: 1.40(1H,m), 1.60(1H,m), 182(1H,m), 2.12(3H,m), 2.47–2.65(5H), 2.78(1H,m), 3.34(1H, d, J=12), 3.59(4H,s), 3.87(1H,m), 5.31(1H, d, J=12), 6.81(1H,m), 6.96(2H,m), 7.11(3H,m), 7.18–7.36(12H); FABMS(m/z): 520(M)⁺

Example 7

5,11-dihydro-5-[1-(pyridin-4-yl)methylpiperidin-4-yl]-dibenz[b,e][1,4]thiazepine ¹HNMR(CDCl₃)δ: 1.50(1H,m), 172(1H,m), 1.88(1H,m), 2.19(3H,m), 2.62(1H,m), 2.83(1H,m), 3.36(1H, d, J=12), 3.52(2H,s), 3.95(1H,m), 5.31(1H, d, J=12), 6.82(1H,m), 6.98(2H,m), 7.13(3H,m), 7.20–7.31(4H,m), 8.51(2H, dd, J=1.7, 4.7) ESIMS(m/z):388(M+H)⁺

Example 8

5,11-dihydro-5-[1-(2-ethoxycarbonyl)ethylpiperidin-4-yl]-dibenz[b,e][1,4]thiazepine ¹HNMR(CDCl₃)δ: 1.25(3H, t, J=7.2), 1.45(1H,m), 1.68 (1H,m), 188 (1H,m), 2.19(3H,m), 2.50(2H, t, J=3.8), 2.69 (3H,m), 2.86(1H,m), 3.36(1H, d, J=12), 3.92(1H,m), 4.13 (2H,q,J=7.2), 5.33(1H,d,J=12), 6.82(1H,m), 6.99(1H,m), 7.12(3H,m), 7.24(1H,m), 7.31(1H,m); EIMS(m/z):396(M)⁺

Example 9

5,11-dihydro-5-[1-(thiophen-2-yl)methylpiperidin-4-yl]-dibenz[b,e][1,4]thiazepine ¹HNMR(CDCl₃)δ: 1.50(1H,m), 1.71(1H,m), 1.87(1H,m), 2.13–2.30 (3H,m), 2.68(1H,m), 2.92(1H,m), 3.33(1H, d, J=12), 3.75(2H,s), 3.93(1H,m), 5.28(1H, d, J=12), 6.81(1H, m), 6.86–7.00(4H,m), 7.12(3H,m), 7.19–7.31(3H,m); ESIMS(m/z): 393(M+H)⁺

Example 10

5,11-dihydro-5-(1-octadecylpiperidin-4-yl)dibenz-[b,e][1,4]thiazepine

¹HNMR(CDCl₃)δ: 0.88(3H,t,J=6.7), 1.24–1.64(34H), 1.90(1H,m), 2.18(3H,m), 2.33(2H,m), 2.68(1H,m), 2.88

(1H,m), 3.37(1H,d,J=12), 3.95(1H,m), 5.33(1H,d,J=12), 6.83(1H,m), 6.99(2H,m), 7.13(3H,m), 7.23(1H,m), 7.30 (1H,dd,J=1.4, 7.5); ESIMS(m/z):549 (M+H)$^+$

Example 11

5-(carbamoylmethylpiperidin-4-yl)-5,11-dihydrodibenz-[b,e][1,4]thiazepine $^1$HNMR(CDCl$_3$)δ: 1.45(1H,m), 1.67(1H,m), 1.90(1H,m), 2.21–2.39(3H,m), 2.72(1H,m), 2.90(1H,m), 3.01(2H,s), 3.39(1H,d,J=12), 3.93(1H,m), 5.30(1H,d,J=12), 5.41(1H, brs), 6.84(1H,m), 7.01(2H,m), 7.15(3H,m), 7.23(1H,m), 7.31(1H,m); ESIMS(m/z):354(M+H)$^+$

Example 12

5,11-dihydro-5-(1-p-fluorobenzylpiperidin-4-yl)dibenz-[b,e][1,4]thiazepine $^1$HNMR(CDCl$_3$)δ: 1.47(1H,m), 1.67(1H,m), 1.85(1H,m), 2.15(3H,m), 2.61(1H,m), 2.82(1H,m), 3.34(1H,d,J=12), 3.48(2H,s), 3.92(1H,m), 5.29(1H,d,J=12), 6.80–7.27(12H); ESIMS(m/z):405(M+H)$^+$

Example 13

5,11-dihydro-5-[1-(3-methoxy-2-nitro)cinnamylpiperidin-4-yl]dibenz[b,e][1,4]thiazepine $^1$HNMR(CDCl$_3$)δ: 1.47(1H,m), 1.68(1H,m), 1.89(1H,m), 2.18(3H,m), 2.70(1H,m), 2.90(1H,m), 3.15(2H,m), 3.36 (1H,d,J=12.1), 3.88 (3H,s), 3.94(1H,m), 5.34(1H,d,J=12.1), 6.37(2H,m), 6.80–6.91 (2H,m), 6.97–7.01(2H,m), 7.10–7.16(4H,m), 7.21–7.37(3H,m); FABMS(m/z):488 (M+H)$^+$

Example 14

5-(1-carboxyethylpiperidin-4-yl)-5,11-dihydrodibenz-[b,e][1,4]thiazepine

To a solution of the compound of Example 8 (166 mg) in ethanol (1 ml) was added a 1N aqueous sodium hydroxide solution (0.54 ml), and the mixture was stirred at a room temperature for 2 hours. The reaction was concentrated, dissolved in a small amount of water, and purified by chromatography on a column packed with the adsorption resin HP-20. The resin was washed with water, and then the title compound was obtained by eluting with 10–40% aqueous acetone solution in an amount of 164 mg after lyophilization.

$^1$HNMR(D$_2$O)δ:1.39(1H,m), 1.56(1H,m), 1.82(1H,m), 2.10–2.31(3H,m), 2.36(2H,t,J=8.6), 2.64(2H,t,J=8.6), 2.82 (1H,m), 3.51(1H,d,J=12), 4.08(1H,m), 5.33(1H,d,J=12), 6.90(1H,m), 7.04(1H,d d,J=1.4,8.0), 7.11(1H,m), 7.20(1H, m), 7.28–7.34(3H,m), 7.39(1H,m); ESIMS(m/z):369(M+H)$^+$

Pharmacological Test Example
Ischemic Reperfusion Arrhythmic Model Rat

After SD rats (200–300 g body weight) were anesthetized with petobarbital, left and right femoral arteries were peeled for measuring blood pressure and administering drugs. Electrocardiogram by the induction at stage II was recorded at the same time. After a respirator was attached, heart was exposed by thoracotomy followed by pericardiotomy. After ligation of the proximal end of left anterior descending branch for 5 minutes, it was perfused again for 10 minutes to evaluate the effects of the present compound on the incidence of premature contraction, ventricular tachycardia and ventricular fibrillation during the reperfusion, and the mortality. The test compound was dissolved in a solution containing 2.5% HCO-60 and 2.5% ethanol, administered once at 5 minutes before ligation and then continuously infused until the end of reperfusion.

The compound of Example 13 descreased the incidence of arrhythmia and the mortality in a dose of 0.1 –1.0 mg/kg. This result shows that the compound according to the present invention has antiarrhythmic activity.

The compounds of Examples 1–14 represented by formula (I) are listed on Table 1.

TABLE 1

| | Q | R$^1$ | R$^2$ | m | n | A |
|---|---|---|---|---|---|---|
| 1 | S | H | H | 0 | 0 | H |
| 2 | S | H | H | 4 | 0 | 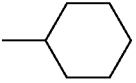 |
| 3 | S | H | H | 1 | 0 | 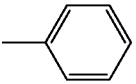 |
| 4 | S | H | H | 1 | 1 | 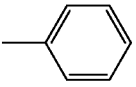 |
| 5 | S | H | H | 2 | 0 | 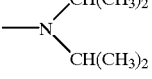 |
| 6 | S | H | H | 2 | 0 | 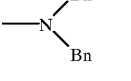 |
| 7 | S | H | H | 1 | 0 | 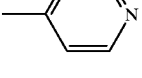 |
| 8 | S | H | H | 2 | 0 | —COOCH$_2$CH$_3$ |
| 9 | S | H | H | 1 | 0 | 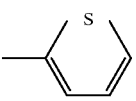 |
| 10 | S | H | H | 18 | 0 | H |
| 11 | S | H | H | 1 | 0 | —CONH$_2$ |
| 12 | S | H | H | 1 | 0 |  |
| 13 | S | H | H | 1 | 1 | 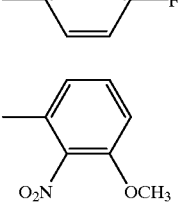 |
| 14 | S | H | H | 2 | 0 | —COOH |

We claim:
1. A compound of formula (I):

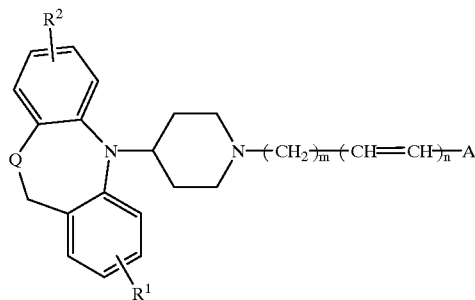

(I)

wherein
R¹ and R², which may be the same or different, each represent hydrogen, halogen or lower alkyl which may be substituted by halogen;
A represents hydrogen, $C_{3-6}$ cycloalkyl, phenyl, a saturated or unsaturated 5-membered or 6-membered heterocyclic group which may contain one or more heteroatoms selected from a nitrogen, sulphur and oxygen atom, —NR³R⁴ (wherein R³ and R⁴, which may be the same or different, each represent hydrogen or lower alkyl which may be substituted by halogen or phenyl), or —COR⁵ (wherein R⁵ represents hydroxyl, amino or lower alkoxy which may be substituted by halogen), and where the $C_{3-6}$ cycloalkyl group, the phenyl group and the heterocyclic group each may be substituted by one or more substituents selected from halogen, nitro, and lower alkoxy which may be substituted by halogen;
Q represents an oxygen or sulphur atom;
m represents an integer from 0 to 18; and
n represents zero, 1 or 2,
or pharmaceutically acceptable salts or solvates thereof.

2. A compound of claim 1 wherein R¹ and R² each represent hydrogen.

3. A compound of claim 1 wherein A represents hydrogen, cyclohexyl, phenyl, p-fluorophenyl, (3-methoxy-2-nitro)phenyl, pyridinyl, thiophenyl, —N(CH(CH₃)₂)₂, —N(Bn)₂ (wherein Bn represents benzyl), —COOH, —COOCH₂CH₃, or —CONH₂.

4. A compound of claim 1 wherein Q is a sulphur atom.

5. A compound of claim 1 wherein
A represents hydrogen, $C_{3-6}$ cycloalkyl, phenyl which may be substituted by one or more substituents selected from halogen, nitro, and lower alkoxy, a saturated or unsaturated 5-membered or 6-membered heterocyclic ring which may contain a nitrogen or sulphur atom or a combination thereof, —NR³R⁴ (wherein R³ and R⁴, which may be the same or different, each represent hydrogen or lower alkyl which may be substituted by phenyl), or COR⁵ (wherein R⁵ represents hydroxyl, amino or lower alkoxy);
Q represents a sulphur atom;
m represents an integer from 0 to 18; and
n represents zero, 1 or 2.

6. A compound selected from the group consisting of:
(1) 5-(piperidin-4-yl)-5,11-dihydrodibenz[b,e][1,4]thiazepine,
(2) 5-[1-(4-cyclohexyl-1-butyl)piperidin-4-yl]-5,11-dihydrodibenz [b,e][1,4]thiazepine,
(3) 5-(1-benzylpiperidin-4-yl)-5,11-dihydrodibenz[b,e][1,4]-thiazepine,
(4) 5-(1-cinnamylpiperidin-4-yl)-5,11-dihydrodibenz[b,e][1,4]-thiazepine,
(5) 5,11-dihydro-5-[1-(N,N-di-iso-propylaminoethyl)piperidin-4-yl]dibenz[b,e][1,4]thiazepine,
(6) 5,11-dihydro-5-[1-(N,N-dibenzylaminoethyl)piperidin-4-yl]-dibenz[b,e][1,4]thiazepine,
(7) 5,11-dihydro-5-[1-(pyridin-4-yl)methylpiperidin-4-yl]-dibenz[b,e][1,4]thiazepine,
(8) 5,11-dihydro-5-[1-(2-ethoxycarbonyl)ethylpiperidin-4-yl]-dibenz[b,e][1,4]thiazepine,
(9) 5,11-dihydro-5-[1-(thiophen-2-yl)methylpiperidin-4-yl]-dibenz[b,e][1,4]thiazepine,
(10) 5,11-dihydro-5-(1-octadecylpiperidin-4-yl)dibenz-[b,e][1,4]thiazepine,
(11) 5-(carbamoylmethylpiperidin-4-yl)-5,11-dihydrodibenz-[b,e][1,4]thiazepine,
(12) 5,11-dihydro-5-(1-p-fluorobenzylpiperidin-4-yl) dibenz-[b,e][1,4]thiazepine,
(13) 5,11-dihydro-5-[1-(3-methoxy-2-nitro)cinnamylpiperidin-4-yl]dibenz[b,e][1,4]thiazepine, and
(14) 5-(1-carboxyethylpiperidin-4-yl)-5,11-dihydrodibenz-[b,e][1,4]thiazepine, or pharmaceutically acceptable salts or solvates thereof.

7. A pharmaceutical composition comprising a compound of claim 1 or pharmaceutically acceptable salt or solvate thereof, and a pharmaceutically acceptable carrier.

8. A method for the treatment of arrhythmia comprising administration of an effective amount of a compound of claim 1 or pharmaceutically acceptable salt or solvate thereof together with a pharmaceutically acceptable carrier to a mammal in need of said treatment.

9. A method of claim 8 wherein the mammal is a human.

* * * * *